(12) United States Patent
Spilker et al.

(10) Patent No.: US 8,200,466 B2
(45) Date of Patent: Jun. 12, 2012

(54) METHOD FOR TUNING PATIENT-SPECIFIC CARDIOVASCULAR SIMULATIONS

(75) Inventors: Ryan Leonard Spilker, Stanford, CA (US); Chales Anthony Taylor, Jr., Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 651 days.

(21) Appl. No.: 12/219,398

(22) Filed: Jul. 21, 2008

(65) Prior Publication Data

US 2010/0017171 A1    Jan. 21, 2010

(51) Int. Cl.
G06F 7/60 (2006.01)
G06F 17/10 (2006.01)
G06G 7/50 (2006.01)
G06G 7/58 (2006.01)

(52) U.S. Cl. .................. 703/11; 703/2; 703/9
(58) Field of Classification Search .................. 703/2, 9, 703/11
See application file for complete search history.

(56) References Cited

U.S. PATENT DOCUMENTS

| | | |
|---|---|---|
| 5,119,816 A | 6/1992 | Gevins |
| 5,151,856 A | 9/1992 | Halmann et al. |
| 5,205,289 A | 4/1993 | Hardy et al. |
| 5,235,510 A | 8/1993 | Yamada et al. |
| 5,582,173 A | 12/1996 | Li |
| 5,682,886 A | 11/1997 | Delp et al. |
| 5,687,208 A | 11/1997 | Bae et al. |
| 5,687,737 A | 11/1997 | Branham et al. |
| 5,729,670 A | 3/1998 | Strumolo et al. |
| 5,740,802 A | 4/1998 | Nafis et al. |
| 5,782,762 A | 7/1998 | Vining |
| 5,825,908 A | 10/1998 | Pieper et al. |
| 5,871,018 A | 2/1999 | Delp et al. |
| 5,920,319 A | 7/1999 | Vining et al. |
| 5,947,899 A | 9/1999 | Winslow et al. |
| 6,026,173 A | 2/2000 | Svenson et al. |
| 6,047,080 A | 4/2000 | Chen et al. |

(Continued)

FOREIGN PATENT DOCUMENTS

EP    0 559 919 A1    9/1993

(Continued)

OTHER PUBLICATIONS

Santamarina, Aland, et al., "Computational Analysis of Flow in a Curved Tube Model of the Coronary Arteries: Effects of Time-Varying Curvature," Annals of Biomedical Engineering, 1998, 26:944-954.

(Continued)

*Primary Examiner* — David Silver
(74) *Attorney, Agent, or Firm* — Finnegan, Henderson, Farabow, Garrett & Dunner LLP

(57) ABSTRACT

Computational methods are used to create cardiovascular simulations having desired hemodynamic features. Cardiovascular modeling methods produce descriptions of blood flow and pressure in the heart and vascular networks. Numerical methods optimize and solve nonlinear equations to find parameter values that result in desired hemodynamic characteristics including related flow and pressure at various locations in the cardiovascular system, movements of soft tissues, and changes for different physiological states. The modeling methods employ simplified models to approximate the behavior of more complex models with the goal of to reducing computational expense. The user describes the desired features of the final cardiovascular simulation and provides minimal input, and the system automates the search for the final patient-specific cardiovascular model.

31 Claims, 1 Drawing Sheet

U.S. PATENT DOCUMENTS

| | | | |
|---|---|---|---|
| 6,083,162 A | 7/2000 | Vining | |
| 6,117,087 A | 9/2000 | Kramm | |
| 6,169,917 B1 | 1/2001 | Masotti et al. | |
| 6,176,838 B1 | 1/2001 | Sase | |
| 6,236,878 B1 | 5/2001 | Taylor | |
| 6,272,366 B1 | 8/2001 | Vining | |
| 6,278,460 B1 | 8/2001 | Myers et al. | |
| 6,366,800 B1 | 4/2002 | Vining et al. | |
| 6,379,041 B1 | 4/2002 | Schuetz et al. | |
| 6,381,562 B2 | 4/2002 | Keane | |
| 6,442,235 B2 | 8/2002 | Koppe et al. | |
| 6,466,205 B2 | 10/2002 | Simpson et al. | |
| 6,487,432 B2 | 11/2002 | Slack | |
| 6,501,848 B1 | 12/2002 | Carroll et al. | |
| 6,606,091 B2 | 8/2003 | Liang et al. | |
| 6,628,743 B1 | 9/2003 | Drummond et al. | |
| 6,650,724 B2 | 11/2003 | Strobel | |
| 6,666,820 B1 | 12/2003 | Poole | |
| 6,694,163 B1 | 2/2004 | Vining | |
| 6,711,433 B1 | 3/2004 | Geiger et al. | |
| 6,718,004 B2 | 4/2004 | Cesmeli | |
| 6,720,966 B2 | 4/2004 | Barth et al. | |
| 6,793,496 B2 | 9/2004 | Edic et al. | |
| 6,801,643 B2 | 10/2004 | Pieper | |
| 6,898,453 B2 | 5/2005 | Lee | |
| 6,909,913 B2 | 6/2005 | Vining | |
| 6,932,842 B1 | 8/2005 | Litschko et al. | |
| 6,950,689 B1 | 9/2005 | Willis et al. | |
| 6,996,262 B2 | 2/2006 | Li | |
| 7,006,955 B2 * | 2/2006 | Daft et al. | 703/5 |
| 7,121,832 B2 | 10/2006 | Hsieh et al. | |
| 7,149,333 B2 | 12/2006 | Pieper et al. | |
| 7,149,564 B2 | 12/2006 | Vining et al. | |
| 7,182,602 B2 * | 2/2007 | Lakin et al. | 434/262 |
| 7,191,110 B1 | 3/2007 | Charbel | |
| 7,229,412 B2 | 6/2007 | Jacob et al. | |
| 7,286,866 B2 | 10/2007 | Okerlund et al. | |
| 7,302,286 B2 | 11/2007 | Camus et al. | |
| 7,321,677 B2 | 1/2008 | Evron et al. | |
| 7,327,862 B2 | 2/2008 | Murphy et al. | |
| 7,333,643 B2 | 2/2008 | Murphy et al. | |
| 7,333,648 B2 | 2/2008 | Edic et al. | |
| 7,343,196 B2 | 3/2008 | Okerlund et al. | |
| 7,356,367 B2 | 4/2008 | Liang et al. | |
| 7,369,691 B2 | 5/2008 | Kondo et al. | |
| 7,371,067 B2 | 5/2008 | Anderson et al. | |
| 7,462,153 B2 | 12/2008 | Bostian et al. | |
| 7,474,776 B2 | 1/2009 | Kaufman et al. | |
| 7,505,551 B2 | 3/2009 | Grass et al. | |
| 7,526,112 B2 | 4/2009 | Murphy et al. | |
| 7,536,042 B2 | 5/2009 | Murphy et al. | |
| 7,539,529 B2 | 5/2009 | Schmitt et al. | |
| 7,542,595 B2 | 6/2009 | Moreau-Gobard | |
| 7,574,026 B2 | 8/2009 | Rasche et al. | |
| 7,646,900 B2 | 1/2010 | Movassaghi et al. | |
| 7,646,901 B2 | 1/2010 | Murphy et al. | |
| 7,693,563 B2 | 4/2010 | Suresh et al. | |
| 7,725,164 B2 | 5/2010 | Suurmond et al. | |
| 7,725,165 B2 | 5/2010 | Chen et al. | |
| 7,738,626 B2 | 6/2010 | Weese et al. | |
| 7,739,090 B2 | 6/2010 | Charbel et al. | |
| 7,742,629 B2 | 6/2010 | Zarkh et al. | |
| 7,747,055 B1 | 6/2010 | Vining et al. | |
| 7,751,984 B2 | 7/2010 | Tang | |
| 7,773,719 B2 | 8/2010 | Galant et al. | |
| 7,773,785 B2 | 8/2010 | Murphy et al. | |
| 7,792,565 B2 | 9/2010 | Vining | |
| 7,792,593 B2 | 9/2010 | Rahn et al. | |
| 7,805,177 B2 | 9/2010 | Chen et al. | |
| 7,813,785 B2 | 10/2010 | Okerlund et al. | |
| 7,853,310 B2 | 12/2010 | Vining et al. | |
| 2002/0002447 A1 * | 1/2002 | Keane | 703/11 |
| 2002/0035458 A1 | 3/2002 | Kim et al. | |
| 2002/0120431 A1 * | 8/2002 | Keane | 703/11 |
| 2003/0023266 A1 | 1/2003 | Borillo et al. | |
| 2003/0123606 A1 | 7/2003 | Mollus et al. | |
| 2004/0034309 A1 | 2/2004 | Pullan et al. | |
| 2004/0049115 A1 | 3/2004 | Murphy et al. | |
| 2004/0064298 A1 * | 4/2004 | Levine | 703/11 |
| 2005/0010105 A1 | 1/2005 | Sra | |
| 2005/0018885 A1 | 1/2005 | Chen et al. | |
| 2005/0043609 A1 | 2/2005 | Murphy et al. | |
| 2005/0131663 A1 * | 6/2005 | Bangs et al. | 703/11 |
| 2005/0272992 A1 | 12/2005 | O'Donnell et al. | |
| 2006/0142984 A1 | 6/2006 | Weese et al. | |
| 2006/0166176 A1 * | 7/2006 | Lakin et al. | 434/262 |
| 2006/0171585 A1 | 8/2006 | Rinck et al. | |
| 2006/0239528 A1 | 10/2006 | Camus et al. | |
| 2006/0241445 A1 | 10/2006 | Altmann et al. | |
| 2006/0241461 A1 | 10/2006 | White et al. | |
| 2006/0253024 A1 | 11/2006 | Altmann et al. | |
| 2006/0278245 A1 | 12/2006 | Gan | |
| 2007/0014452 A1 | 1/2007 | Suresh et al. | |
| 2007/0078325 A1 | 4/2007 | Fuimaono et al. | |
| 2007/0219448 A1 | 9/2007 | Seip et al. | |
| 2007/0231779 A1 | 10/2007 | Santhanam et al. | |
| 2007/0238999 A1 | 10/2007 | Specht | |
| 2007/0293936 A1 | 12/2007 | Dobak, III | |
| 2008/0004508 A1 | 1/2008 | Sun et al. | |
| 2008/0020362 A1 * | 1/2008 | Cotin et al. | 434/267 |
| 2008/0040087 A1 | 2/2008 | Watrous | |
| 2008/0118122 A1 | 5/2008 | Sirohey et al. | |
| 2008/0177172 A1 | 7/2008 | John et al. | |
| 2008/0205722 A1 | 8/2008 | Schaefer et al. | |
| 2008/0208068 A1 | 8/2008 | Robertson et al. | |
| 2008/0228086 A1 | 9/2008 | Ilegbusi et al. | |
| 2008/0262346 A1 | 10/2008 | Assis et al. | |
| 2008/0262814 A1 | 10/2008 | Zheng et al. | |
| 2008/0269611 A1 | 10/2008 | Pedrizzetti et al. | |
| 2008/0270095 A1 | 10/2008 | Lombaert et al. | |
| 2008/0275336 A1 | 11/2008 | Deschamps et al. | |
| 2008/0294038 A1 | 11/2008 | Weese et al. | |
| 2008/0317310 A1 | 12/2008 | Suresh et al. | |
| 2008/0319308 A1 * | 12/2008 | Tang | 600/416 |
| 2009/0016483 A1 | 1/2009 | Kawasaki et al. | |
| 2009/0054774 A1 | 2/2009 | Njemanze | |
| 2009/0156933 A1 | 6/2009 | Gerard et al. | |
| 2009/0161938 A1 | 6/2009 | Shekhar et al. | |
| 2009/0177454 A1 | 7/2009 | Bronstein et al. | |
| 2009/0281423 A1 | 11/2009 | Sirohey et al. | |
| 2009/0281434 A1 | 11/2009 | Messerges | |
| 2009/0292206 A1 | 11/2009 | Sato | |
| 2009/0310840 A1 | 12/2009 | Mohamed et al. | |
| 2009/0324052 A1 | 12/2009 | Nowinski | |
| 2010/0053209 A1 | 3/2010 | Rauch et al. | |
| 2010/0070249 A1 | 3/2010 | Ionasec et al. | |
| 2010/0081917 A1 | 4/2010 | Zhang et al. | |
| 2010/0086099 A1 | 4/2010 | Kuzmanovic | |
| 2010/0130878 A1 | 5/2010 | Lasso et al. | |
| 2010/0152570 A1 | 6/2010 | Navab | |
| 2010/0156898 A1 | 6/2010 | Voros et al. | |
| 2010/0183206 A1 | 7/2010 | Carlsen et al. | |
| 2010/0189337 A1 | 7/2010 | Jandt et al. | |
| 2010/0241404 A1 | 9/2010 | Taylor et al. | |
| 2010/0265251 A1 | 10/2010 | Vining et al. | |
| 2010/0266176 A1 | 10/2010 | Masumoto et al. | |
| 2010/0272315 A1 | 10/2010 | Tsin et al. | |
| 2010/0280352 A1 | 11/2010 | Ionasec et al. | |
| 2010/0298719 A1 | 11/2010 | Kock et al. | |
| 2010/0328305 A1 | 12/2010 | Vining | |
| 2011/0152599 A1 * | 6/2011 | Bokeriya et al. | 600/16 |

FOREIGN PATENT DOCUMENTS

| | | | |
|---|---|---|---|
| EP | 1 182 619 A2 | 2/2002 | |
| EP | 1 225 541 A2 | 7/2002 | |
| EP | 1 482 470 A2 | 12/2004 | |
| EP | 1 492 071 A1 | 12/2004 | |
| EP | 0 961 993 B1 | 2/2005 | |
| EP | 1 717 758 A2 | 11/2006 | |
| EP | 1 717 759 A1 | 11/2006 | |
| EP | 1 961 384 A1 | 8/2008 | |
| EP | 1 967 140 A1 | 9/2008 | |
| EP | 2 028 608 A2 | 2/2009 | |
| EP | 2 138 091 A1 | 12/2009 | |
| EP | 2 302 594 A2 | 3/2011 | |
| EP | 2 302 595 A2 | 3/2011 | |
| EP | 2 302 596 A1 | 3/2011 | |

| | | | |
|---|---|---|---|
| WO | WO 94/08315 A1 | 4/1994 |
| WO | WO 95/26682 A1 | 10/1995 |
| WO | WO 96/38815 A1 | 12/1996 |
| WO | WO 96/41567 A2 | 12/1996 |
| WO | WO 97/17894 A1 | 5/1997 |
| WO | WO 97/49065 A1 | 12/1997 |
| WO | WO 98/11524 A1 | 3/1998 |
| WO | WO 98/32371 A1 | 7/1998 |
| WO | WO 98/43201 A1 | 10/1998 |
| WO | WO 99/38433 A1 | 8/1999 |
| WO | WO 99/42977 A1 | 8/1999 |
| WO | WO 99/63887 A1 | 12/1999 |
| WO | WO 00/07501 A1 | 2/2000 |
| WO | WO 00/32106 A1 | 6/2000 |
| WO | WO 00/55812 A1 | 9/2000 |
| WO | WO 00/55814 A2 | 9/2000 |
| WO | WO 00/68749 A1 | 11/2000 |
| WO | WO 00/72272 A1 | 11/2000 |
| WO | WO 01/22362 A1 | 3/2001 |
| WO | WO 01/85030 A1 | 11/2001 |
| WO | WO 02/29764 A1 | 4/2002 |
| WO | WO 02/095686 A1 | 11/2002 |
| WO | WO 03/034336 A2 | 4/2003 |
| WO | WO 03/060553 A2 | 7/2003 |
| WO | WO 03/081529 A1 | 10/2003 |
| WO | WO 2004/010374 A2 | 1/2004 |
| WO | WO 2004/012152 A2 | 2/2004 |
| WO | WO 2004/066807 A2 | 8/2004 |
| WO | WO 2004/068406 A2 | 8/2004 |
| WO | WO 2004/072903 A2 | 8/2004 |
| WO | WO 2005/004038 A1 | 1/2005 |
| WO | WO 2005/004721 A1 | 1/2005 |
| WO | WO 2005/027765 A1 | 3/2005 |
| WO | WO 2005/031635 A1 | 4/2005 |
| WO | WO 2005/083633 A2 | 9/2005 |
| WO | WO 2005/119578 A2 | 12/2005 |
| WO | WO 2006/002353 A2 | 1/2006 |
| WO | WO 2006/020920 A2 | 2/2006 |
| WO | WO 2006/061815 A1 | 6/2006 |
| WO | WO 2006/066122 A2 | 6/2006 |
| WO | WO 2006/079042 A2 | 7/2006 |
| WO | WO 2006/082558 A2 | 8/2006 |
| WO | WO 2007/020555 A2 | 2/2007 |
| WO | WO 2007/066249 A2 | 6/2007 |
| WO | WO 2007/102858 A1 | 9/2007 |
| WO | WO 2008/030192 A1 | 3/2008 |
| WO | WO 2009/007910 A2 | 1/2009 |
| WO | WO 2009/056147 A1 | 5/2009 |

OTHER PUBLICATIONS

Boutsianis, Evangelos, et al., "Computational Simulation of Intracoronary Flow Based on Real Coronary Geometry," European Journal of Cardio-thoracic Surgery, 2004, 26:248-256.

Quarteroni, Alfio, et al., "Coupling Between Lumped and Distributed Models for Blood Flow Problems," Comput Visual Sci, 2001, 4:111-124.

Berry, Joel L., et al., "Experimental and Computational Flow Evaluation of Coronary Stents," Annals of Biomedical Engineering, 2000, 28:386-398.

Myers, J.G., et al., "Factors Influencing Blood Flow Patterns in the Human Right Coronary Artery," Annals of Biomedical Engineering, 2001, 29:109-120.

Lagana, Katia, et al., "Multiscale Modeling of the Cardiovascular System: Application to the Study of Pulmonary and Coronary Perfusions in the Univentricular Circulation," Journal of Biomechanics, 2005, 38:1129-1141.

Qiu, Yuchen, et al., "Numerical Simulation of Pulsatile Flow in a Compliant Curved Tube Model of a Coronary Artery," Journal of Biomechanical Engineering, 2000, 122:77-85.

Formaggia, L., et al., "Numerical Treatment of Defective Boundary Conditions for the Navier-Stokes Equations," SIAM J. Numer. Anal., 2002, 40(1):376-401.

Gijsen, Frank J.H., et al., "Strain Distribution Over Plaques in Human Coronary Arteries Relates to Shear Stress," Am J Physiol Heart Circ Physiol, 2008, 295:H1608-H1614.

Perktold, K., et al., "Validated Computation of Physiologic Flow in a Realistic Coronary Artery Branch," Journal of Biomechanics, 1998, 31:217-228.

Spilker, Ryan L., et al., "Tuning Hemodynamic Simulations With Three-Element Windkessel Outlet Boundary Conditions," Jul. 24, 2007, 32 pages.

Taylor, Charles A., et al., "Predictive Medicine: Computational Techniques in Therapeutic Decision-Making," Computer Aided Surgery, 1999, 4:231-247.

Taylor, Charles A., et al., "Computational Investigations in Vascular Disease," Computers in Physics, vol. 10, No. 3, May/Jun. 1996, pp. 224-232.

Taylor, Charles A., "A Computational Framework for Investigating Hemodynamic Factors in Vascular Adaptation and Disease," Aug. 1996, 118 pages.

Wang, Kenneth C., "Improving Geometric Model Construction for Blood Flow Modeling," IEEE Engineering in Medicine and Biology, Nov./Dec. 1999, pp. 33-39.

Ellwein et al. Cardiovasc Eng (2008) 8:73-87. DOI 10.1007/s10558-007-9050-8.

Spilker et al., Ann Biomed Eng (2007) 35:546-559. DOI 10.1007/s10439-006-9240-3.

Ryan L. Spilker et al. Presentation, 9th US Nat'l Congress on Computational Mechanics, Jul. 27, 2007.

* cited by examiner

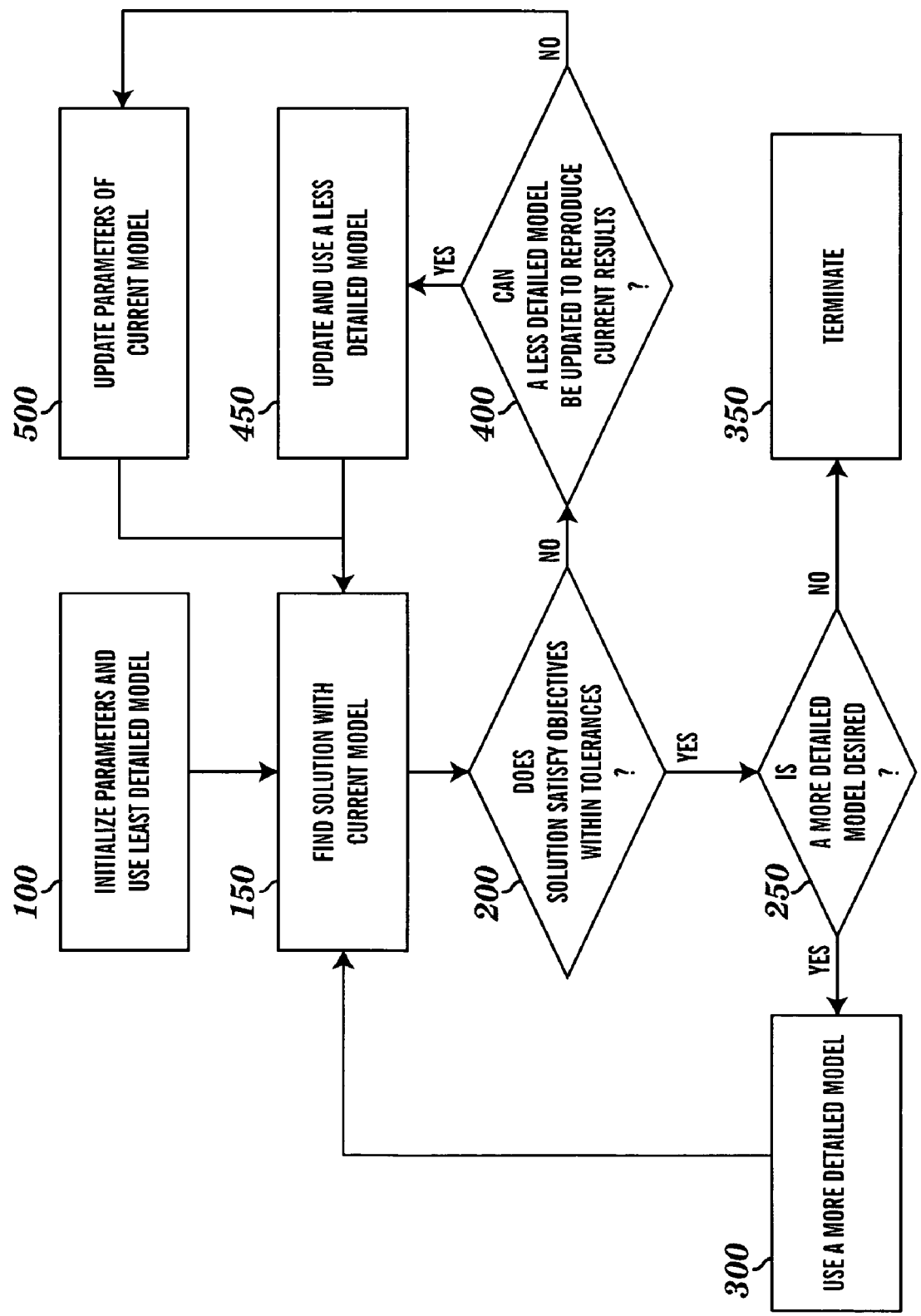

METHOD FOR TUNING PATIENT-SPECIFIC CARDIOVASCULAR SIMULATIONS

STATEMENT REGARDING FEDERAL RIGHTS

This invention was made in part with government support under Grant Number 0205741 awarded by the National Science Foundation.

BACKGROUND OF THE INVENTION

1. Field of the Invention

This invention relates generally to computer-assisted modeling and planning systems and in particular to a computer-assisted human anatomic and physiologic modeling system used to predict outcomes of medical intervention and further to predict changes in physiologic function under various states, stresses, and environments and still further to generate data for disease research or medical device design.

2. Discussion of Prior Art

Disclosed in Kamm et al., U.S. Pat. No. 6,117,087, is a method and apparatus for deriving a physiological description and clinically-useful data regarding the cardiovascular system of an individual subject. The method includes obtaining a measurement sample associated with cardiovascular flow and utilizing a model, which may be distributed and/or non-linear to derive a description and data. The model generates and uses functions of source parameters and may, in an embodiment, match measurement samples against a library of stored, predicted samples. A best-matching, predicted sample may then be associated with a measurement sample. An apparatus is provided that, according to an embodiment, includes an input for obtaining a measurement sample, a processor to derive the description and data, and an output. The apparatus may also include a digital storage medium to store a library of predicted samples.

Disclosed in Taylor et al., U.S. Pat. No. 6,236,878, is a method for predictive modeling of human anatomy and physiologic function for planning medical interventions on at least one portion of a body with the goals of improving the outcome of the medical intervention and reducing the risks associated with medical intervention. The method comprises the steps of generation of multi-dimensional continuous geometric models of human anatomy, the generation of models of physiologic functions, the integration of the multi-dimensional continuous geometric human anatomy models with the physiologic functional models, and the use of the integrated models to predict the outcome of medical interventions. Also disclosed is a method for the integration of multi-dimensional continuous geometric models of human anatomy and models of physiologic functions to evaluate and predict changes in physiologic function in various functional states, stresses and environments and a method for generating data for disease research.

A method and apparatus for modeling circulation in a living subject is disclosed in Charbel et al, U.S. Pat. No. 7,191,110. The method includes the steps of developing a model for living subjects in general and correcting the model to substantially conform to the overall cerebral physiology of the living subject. The method further includes the step of calculating a cerebral flow of the living subject based upon the corrected model and a selected cerebral blood flow perturbation.

The paper by Spilker et al., Ann Biomed Eng (2007) 35:546-559. DOI 10.1007/s10439-006-9240-3, demonstrates the tuning of a model of pulmonary arterial hemodynamics with morphometry-based impedance outlet boundary conditions. A reduced-order model using steady flow was used to help initialize the tuning of a mean flow fraction and mean pressure of a more detailed model.

The paper by Ellwein et al., Cardiovasc Eng (2008) 8:73-87. DOI 10.1007/s10558-007-9050-8, describes a search for parameter values for unsteady cardiovascular simulations. This work involved tuning lumped-parameter models and, more specifically, models that were reduced to systems of ordinary differential equations (ODE's), which were solved with numerical methods for temporal integration of ODE's. An effort was made to identify the parameters to which the cardiovascular model was most sensitive.

This invention incorporates tuning of reduced-order models of unsteady cardiovascular dynamics and, in addition, reduced-order models that can be solved more quickly using Fourier analysis. In addition, this invention provides the framework for tuning features of time-varying hemodynamic simulations that allows the user to choose either a single objective function that combines many objectives, as in the work of Ellwein et al., or a set of objectives of the same size as the set of parameters so that a solution of a nonlinear system can be sought. This novel use of a limited set of features of the hemodynamic simulations as objectives can give the user control over the most important aspects of the simulation and may save computational energy.

A key difference between this invention and Kamm et al. U.S. Pat. No. 6,117,087, Taylor et al. U.S. Pat. No. 6,236,878, Charbel et al. U.S. Pat. No. 7,191,110, and the work of Ellwein et al. is this invention's use of these less detailed models in the process of tuning hemodynamic simulations that are significantly more computationally expensive. This difference makes this invention most valuable when implemented in software for modeling blood flow in three dimensions for the purposes of intervention planning, disease research and medical device design and evaluation. Previous work does not describe time-varying hemodynamic models of various degrees of complexity and their connection to one another. This aspect of this invention, along with the automation of the tuning process, will save users and computers significant time and effort.

SUMMARY OF THE INVENTION

Cardiovascular models have the potential to improve our understanding of the mechanics of the circulatory system in healthy and diseased states and to provide quantitative predictions of the outcomes of various interventions to aid in planning treatments. In order to serve this purpose, hemodynamic simulations must have the ability to faithfully represent a patient's circulation prior to treatment. Recent advances in the fidelity of hemodynamic simulations include the use of anatomic models constructed from medical image data, deformation of vascular walls, and improved representation of downstream vascular beds using appropriate outlet boundary conditions. This invention provides a method for employing these capabilities, enabling the systematic tuning of a hemodynamic simulation's parameters such that its hemodynamic characteristics match more than simply patient-specific vascular geometry, inlet flow, mean flow rates, and mean pressures.

BRIEF DESCRIPTION OF THE DRAWING

FIG. 1 is a flow chart illustrating an embodiment of the method of the present invention for tuning patient-specific hemodynamic simulations.

DETAILED DESCRIPTION

The present invention applies computational methods to create cardiovascular simulations having desired hemodynamic features. A variety of cardiovascular modeling methods can be used to produce descriptions of time-varying blood flow and pressure in the heart and vascular networks. Numerical methods for optimization and solution of nonlinear systems of equations are used to find values for the parameters used in such models that result in simulations that match desired hemodynamic characteristics. These characteristics will often be those of the cardiovascular system of a particular subject. A variety of modeling methods are used for the same cardiovascular system such that more simplified models can be used to approximate the behavior of more detailed and complex models, which may lead to reduced computational expense. A system is created from these methods such that the user describes the desired features of the final cardiovascular simulation and provides minimal input, and the system automates the search for the final cardiovascular model.

Embodiments of this invention address cardiovascular models with a variety of parameters including, but not limited to, resistances, impedances, compliances, inductances, cardiac chamber elastances, material parameters of tissues, vascular network structures, and changes in these parameters with changes in physiological, disease, and interventional states. Also included are relationships between the various parameters of the models, including time constants defined by combinations of resistances and capacitors in lumped-parameter regions of cardiovascular models.

The desired features, called objectives, of the cardiovascular models addressed by embodiments of this invention include, but are not limited to, features of pressure waveforms, features of flow waveforms, features of time-varying velocity fields, features of transport, features of cardiac volume, features of tissue movements, and variations in these features with changes in physiological, disease, and interventional states. Relevant features of a time-varying quantity include the maximum, minimum, median, mean value over a certain portion of the cardiac cycle, and values at particular times.

The computational expense of solving the mathematical equations associated with a model of the cardiovascular system is generally related to the model's level of detail. The cost of solving these equations for several sets of values of a highly detailed model's parameters can be prohibitive. This motivates the approximation of a highly detailed model's behavior in a model that can be evaluated less expensively. For example, a numerical solution of the mechanics of blood flow and vascular motion in a three-dimensional arterial network with inlet boundary conditions representing the movement of the heart, outlet boundary conditions involving lumped-parameter models that approximate the behavior of downstream vascular networks, and deformable vessel walls has a high computational cost. This model's flow waveforms may be approximated, in an embodiment of this invention, by a lumped-parameter model that includes the inlet and outlet boundary conditions of the complex model and lumped-parameter models that approximate the impedances of the flow pathways from the inlet to the outlets, called intrinsic impedances. The reduced-order model allows testing many values for the lumped parameters of the inlet and outlet boundary conditions with low computational cost and can be used to help find a combination of these values that produces desired hemodynamic features in the highly detailed model. If the successful parameters of the lumped-parameter model do not meet the same success in the highly detailed model, the lumped-parameter model can be adjusted to contain more accurate intrinsic impedances. Other embodiments reduce the intrinsic impedances of the highly detailed model to impedance spectra in the reduced-order model.

Some embodiments of this method rely on less detailed models only to provide an initial estimate of the parameters of the more detailed models that will result in the desired hemodynamic features. Some embodiments use the less detailed models to determine the variations in cardiovascular model outputs with variations in parameter values.

The application of a preferred embodiment of this invention to the tuning of a specific model of blood flow in the abdominal aorta provides an illustrative example of the method disclosed herein. Patient-specific flow waveforms are measured in two locations, one proximal to the celiac bifurcation and one distal to the renal arteries. Maximum and minimum blood pressures are recorded. A detailed model is chosen, consisting of a geometric model of the abdominal aorta and its largest branch vessels, created from medical image data, a highly refined mesh of the geometric model on which the incompressible Navier-Stokes equations are solved in three-dimensions using a finite element method. Vessel wall deformations are modeled. Measured flow is applied at the inlet, and outlet boundary conditions are impedances of three-element windkessel lumped-parameter models. The objectives are the desired maximum, minimum, and median of the pressure waveform, the amplitude and diastolic mean value of the measured infrarenal flow waveform, and the mean flow through the infrarenal plane. A set of parameters is chosen by varying several sets of parameters and observing the resulting changes in flow and pressure waveforms. The model parameters chosen to be tuned are the total resistance of the outlets proximal to the infrarenal plane, the total resistance of the distal outlets, and mean values and ratios of the values of the following two quantities for the three-element windkessels proximal and distal to the plane: the ratio of the proximal resistor to the total resistance and the time constant, defined by the product of the capacitance and the distal resistance. Resistances of the outlet vessels are determined by the total resistance of the region to which they belong and the approximate mean flow fractions found in the literature. The tuning of the boundary condition parameters is formulated as a system of six nonlinear equations in six unknowns, seeking a root where the simulated and measured hemodynamic conditions match. This nonlinear system is solved using a quasi-Newton method where each function evaluation requires one three-dimensional simulation. The Jacobian of this system is updated using a version of Broyden's method in which attention is paid to scaling of the different parameters to distribute the secant updates appropriately. The objectives are evaluated first using a reduced-order model consisting of the impedances of the three-element windkessels in parallel. This lumped-parameter model is solved to determine the initial boundary condition parameters for the three-dimensional model. Three-dimensional simulations are run on a coarse initial mesh with a boundary layer at the vessel wall. When a solution of this model is found, the mesh is further refined, more boundary layers are added, and the tuning continues until the simulation on an adequately refined mesh matches the objectives to a desired tolerance. This example illustrates the tuning of parameters that are related to resistances and capacitances. It also illustrates the use of a lumped-parameter model as a reduced-order model for the more detailed cardiovascular model.

This invention employs a range of levels of detail in cardiovascular models. One possible increase in the level of detail is a change from a model using prescribed flow in a blood vessel to a model using an elastance-based model of a cardiac chamber. This allows the prediction of the reaction of the heart to changes in afterload. Another possible increase in the level of detail comes with a change from a model that can be described by a system of ordinary differential equations that can be solved with Fourier analysis to a model that can be described by a system of ordinary differential equations that must be solved with numerical methods for temporal integration. This may occur when a cardiovascular model with an elastance-based heart model is desired. Increases in the level of detail of cardiovascular models also are associated with a change from a model assuming rigid vascular walls to a model assuming more realistic representations of these walls and, in numerical solutions of partial differential equations governing the cardiovascular system, increasingly refined computational meshes and increasingly complete polynomial bases.

The steps in a preferred embodiment of the method for tuning patient-specific hemodynamic simulations are shown in FIG. 1. The parameters for the least detailed model of the cardiovascular system are initialized 100. This step can be aided by prior knowledge of ranges of values for each parameter of such a model. Next, the solution of the mathematical equations governing the current model is sought 150. This includes the determination of the change in the model's features with changes in the model's parameters. A first determination 200 is made if the solution satisfies the objectives within tolerances. If it does, then a second determination 250 is made if a more detailed model is desired. If one is not, then the method has reached a final solution 350. If the second determination 250 is that a more complex model is needed, then a second model 300 is used wherein the level of detail of the second model is increased. The more complex second model 300 is then solved 150 and the process repeated. If the first determination 200 does not satisfy the objectives within tolerances, a third determination 400 is made if a less detailed model can be updated to reproduce current results. If it can, a third model with a reduced level of detail is updated 450 such that it reproduces, within a reasonable tolerance, the important aspects of the more detailed model's results. The less detailed model is then solved 150. If the third determination 400 is that a less detailed model cannot be updated to reproduce current results, then a new model 500 is created by updating the parameters of the current model 150, and the method is repeated until the method has reached a final solution 350.

In a related embodiment of this invention, a less detailed model that approximates the results of a more detailed cardiovascular model is produced as the final result of the tuning procedure. Less detailed models can be used to succinctly characterize cardiovascular systems and in applications requiring rapid simulations, such as the study of relationships between a model's parameters and its behavior.

Some embodiments of this invention involve evaluation of the appropriateness of parameter sets for achieving objectives of cardiovascular dynamics. Certain sets of parameters are associated with better performance of tuning procedures. Parameter sets to which all components of the objective functions are adequately sensitive are desired. Evaluation of various parameter sets can be performed quickly using representative models with less detail.

This invention solves the problem of making cardiovascular simulations match desired hemodynamic characteristics without excessive and ad hoc user interactions. Systematic tuning is enabled by the formulation of one of several problems. A single objective function can be chosen to summarize the differences between the desired and current features of the cardiovascular model. Embodiments with such a cost function employ optimization methods that minimize this difference. In other embodiments having the same number of parameters as objectives, a solution of a system of nonlinear equations is sought. In other embodiments, a solution of a nonlinear least-squares problem is sought. Numerical methods for solving each of these problems are chosen such that the number of function evaluations is kept low. Finite-difference evaluations of Hessian and Jacobian matrices are reduced, in some embodiments, by use of secant updates. Estimates of these matrices are created, in some embodiments, using evaluations of less detailed models.

Highly detailed cardiovascular models may require the use of lumped parameters to represent regions of the cardiovascular system. To aid in the process of choosing parameters for these models without repeated calculation, an embodiment of this invention determines relationships between lumped parameter values and parameters of more detailed distributed cardiovascular models by approximating these more detailed models with lumped-parameter models. The derived relationships can be stored and used by other embodiments to save computational effort.

Several embodiments of the present invention involve analysis of variations of the parameters of cardiovascular models. Patient-specific measurements have natural variations and, when associated with tuned sets of parameters, can provide succinct information about variability of the individual's cardiovascular system. Members of a class of patients can likewise be analyzed for variability within that class of patients. Related embodiments use such information on variability to analyze ranges of potential outcomes of treatments.

The present invention improves upon existing methods by providing a framework for creating state-of-the-art, detailed cardiovascular models that have desired hemodynamic characteristics with methods that automate the procedure and seek to minimize the computational effort. Existing methods use simplified mathematical models or seek to match only temporal mean values of time-varying quantities. Automation of the process allows users to request features of pressure, flow, vascular motion, cardiac motion, and other physiological data and, after providing anatomic and physiological information for the desired cardiovascular model, take no further action while the system produces a mathematical vascular model with the requested results. This capability enables the creation of patient-specific simulations and predictions of the cardiovascular response to various treatments.

Variations can be created from the general approach defined herein. A variety of cardiovascular modeling methods can be used to create the models with various levels of detail and simplifying assumptions. A variety of numerical methods can be used to tune parameters of the cardiovascular models. A variety of sets of hemodynamic objectives and parameters can also be chosen. A variety of algorithms can be chosen to link models of various levels of detail.

In surgical treatment planning, this invention can be used to create cardiovascular models that match hemodynamic features of a specific patient before predicting the results of a variety of surgical options. In medical device development, this invention can be used to create cardiovascular models that match a variety of possible physiological situations to use in simulating the effects of devices on blood flow and pressure or the forces acting on devices that might affect their short-term and long-term safety and efficacy. In cardiovascular tissue engineering, this invention can be used to create cardiovascular models with realistic pressure, flow, and deformation to develop an understanding of the biomechanical environment of tissues.

The present invention allows the user to predict hemodynamic results of interventions without expensive biological experiments thereby reducing user interaction time and computational expense to create realistic cardiovascular models.

We claim:

1. A system for determining cardiovascular information for a patient, the system comprising:
   at least one computer system configured to:
      receive patient-specific data regarding a geometry of an anatomical structure of the patient;
      create, based on the patient-specific data, a three-dimensional model representing at least a portion of the aorta of the patient and at least a portion of a plurality of vessels emanating from the portion of the aorta, the three-dimensional model including portions representing at least one inlet and a plurality of outlets for blood flow;
      create a three-dimensional mesh based on the three-dimensional model;
      create at least one boundary condition model having less than three dimensions, the at least one boundary condition model representing blood flow through at least one of the at least one inlet or the plurality of outlets;
      determine a blood flow characteristic within the anatomical structure of the patient by solving equations governing blood flow using the three-dimensional mesh and the at least one boundary condition model; and
      automatically tune at least one parameter of the three-dimensional model or the at least one boundary condition model.

2. The system of claim 1, wherein the at least one boundary condition model includes at least one resistor configured to characterize flow through at least one of the plurality of outlets.

3. The system of claim 1, wherein the at least one boundary condition model includes at least one impedance model configured to characterize flow through at least one of the plurality of outlets.

4. The system of claim 1, wherein the anatomical structure includes at least a portion of the patient's heart.

5. The system of claim 1, wherein the at least one boundary condition model includes an elastance-based model of a cardiac chamber.

6. The system of claim 1, wherein the at least one computer system is configured to determine the blood flow characteristic in at least the portion of the aorta of the patient and at least the portion of the plurality of vessels emanating from the portion of the aorta.

7. The system of claim 1, wherein a numerical method employed for modifying the at least one parameter includes at least one member of the group consisting of optimization, a solution of a system of nonlinear equations, and a solution of a nonlinear least-squares problem.

8. The system of claim 1, wherein the at least one computer system is further configured to determine the blood flow characteristic based on at least one blood pressure measured in the patient.

9. The system of claim 1, wherein the patient-specific data includes imaging data.

10. The system of claim 1, wherein the blood flow characteristic includes at least one of blood flow or pressure within the anatomical structure of the patient.

11. The system of claim 1, wherein the at least one parameter includes at least one of resistance, impedance, compliance, inductance, cardiac chamber elastance, morphometry of vascular networks, or material parameters of tissue.

12. The system of claim 1, wherein the at least one parameter is automatically tuned in order to bring a determined value of a property of the three-dimensional model or the at least one boundary condition model closer to a desired value.

13. The system of claim 12, wherein the property relates to at least one of a pressure waveform, a flow waveform, a time-varying velocity field, transport, cardiac volume, or tissue movement.

14. The system of claim 12, wherein the at least one computer system is further configured to automatically tune the at least one parameter until a difference between the determined value and the desired value is below a tolerance.

15. The system of claim 12, wherein the desired value is based on a measured parameter.

16. The system of claim 12, wherein the at least one parameter is automatically tuned until a property of the three-dimensional model or the at least one boundary condition model approximates the desired value.

17. The system of claim 1, wherein:
   the at least one boundary condition model includes a plurality of boundary condition models representing blood flow through each of the at least one inlet and the plurality of outlets, respectively; and
   each of the plurality of boundary condition models includes at least one parameter that is automatically tuned.

18. The system of claim 1, wherein the at least one computer system is further configured to change a resolution of the three-dimensional mesh when the at least one parameter is automatically tuned.

19. The system of claim 1, wherein the at least one computer system is further configured to change the at least one boundary condition model when the at least one parameter is automatically tuned.

20. The system of claim 1, wherein:
   the three-dimensional model includes at least one rigid blood vessel wall; and
   the at least one computer system is further configured to replace the at least one rigid blood vessel wall with a less rigid blood vessel wall when the at least one parameter is automatically tuned.

21. The system of claim 1, wherein the at least one computer system is configured to solve the equations using values determined from the three-dimensional mesh and the boundary condition model.

22. A method for determining patient-specific cardiovascular information using at least one computer system, the method comprising:
   inputting into the at least one computer system patient-specific data regarding a geometry of an anatomical structure of the patient;
   creating, using the at least one computer system and based on the patient-specific data, a three-dimensional model representing at least a portion of the aorta of the patient and at least a portion of a plurality of vessels emanating from the portion of the aorta, the three-dimensional model including portions representing at least one inlet and a plurality of outlets for blood flow;
   creating a three-dimensional mesh based on the three-dimensional model;

creating at least one first model having less than three dimensions, the at least one first model representing blood flow through at least one of the at least one inlet or the plurality of outlets;

determining, using the at least one computer system, a blood flow characteristic within the anatomical structure of the patient by solving equations governing blood flow using the three-dimensional mesh and the at least one first model; and creating at least one second model having less than three dimensions, the at least one second model representing at least a portion of the three-dimensional model of the patient and created based on the patient-specific data and on the determined blood flow characteristic.

23. The method of claim 22, wherein the second model includes at least one resistor configured to characterize flow in the second model.

24. The method of claim 22, wherein the second model includes at least one impedance model configured to characterize flow in the second model.

25. The method of claim 22, wherein the blood flow characteristic is determined at a plurality of locations within the anatomical structure of the patient.

26. The method of claim 22, wherein the blood flow characteristic is determined by using a finite element method on the mesh.

27. The method of claim 22, wherein:
the patient-specific data includes imaging data of the patient; and
the three-dimensional mesh represents at least the portion of the aorta of the patient and at least the portion of the plurality of vessels emanating from the portion of the aorta.

28. The method of claim 22, wherein the blood flow characteristic is determined based on a blood pressure measured in the patient.

29. A non-transitory computer readable medium for use on at least one computer system containing computer-executable programming instructions for performing a method for determining patient-specific cardiovascular information, the method comprising:
receiving patient-specific data regarding a geometry of an anatomical structure of the patient;
creating, based on the patient-specific data, a three-dimensional model representing at least a portion of the aorta of the patient and at least a portion of a plurality of vessels emanating from the portion of the aorta, the three-dimensional model including at least one inlet for blood flow and a plurality of outlets for blood flow;
creating a three-dimensional mesh based on the three-dimensional model;
creating at least one boundary condition model having less than three dimensions, the at least one boundary condition model representing blood flow through at least one of the at least one inlet or the plurality of outlets;
determining a blood flow characteristic within the anatomical structure of the patient by solving equations governing blood flow using the three-dimensional mesh and the at least one boundary condition model; and
automatically tuning at least one parameter of the three-dimensional model or the at least one boundary condition model.

30. The non-transitory computer readable medium of claim 29, wherein the at least one boundary condition model includes at least one resistor configured to characterize flow through at least one of the plurality of outlets.

31. The non-transitory computer readable medium of claim 29, the method further comprising:
determining a plurality of mean flow fractions corresponding to the plurality of outlets, wherein the blood flow characteristic is determined based on the plurality of mean flow fractions.

* * * * *

UNITED STATES PATENT AND TRADEMARK OFFICE
CERTIFICATE OF CORRECTION

PATENT NO.        : 8,200,466 B2
APPLICATION NO.   : 12/219398
DATED             : June 12, 2012
INVENTOR(S)       : Ryan L. Spilker et al.

It is certified that error appears in the above-identified patent and that said Letters Patent is hereby corrected as shown below:

On the Title Page, item (75), line 2, "Chales Anthony Taylor, Jr." should read
--Charles Anthony Taylor, Jr.--.

In column 1, lines 6-8, after "National Science Foundation." insert
--The Government has certain rights in the invention.--.

Signed and Sealed this
Seventh Day of August, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,200,466 B2 | |
| APPLICATION NO. | : 12/219398 | |
| DATED | : June 12, 2012 | |
| INVENTOR(S) | : Spilker et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 685 days.

Signed and Sealed this
Fourth Day of September, 2012

David J. Kappos
*Director of the United States Patent and Trademark Office*